United States Patent
Iigaya

(10) Patent No.: US 10,463,045 B2
(45) Date of Patent: Nov. 5, 2019

(54) AGROCHEMICAL COMPOSITION

(71) Applicant: Nippon Soda Co., Ltd., Chiyoda-ku, Tokyo (JP)

(72) Inventor: Masayuki Iigaya, Oyama (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 15/763,157

(22) PCT Filed: Sep. 28, 2016

(86) PCT No.: PCT/JP2016/078594
§ 371 (c)(1),
(2) Date: Mar. 26, 2018

(87) PCT Pub. No.: WO2017/057445
PCT Pub. Date: Apr. 6, 2017

(65) Prior Publication Data
US 2018/0235228 A1    Aug. 23, 2018

(30) Foreign Application Priority Data

Sep. 30, 2015  (JP) .................................. 2015-192835

(51) Int. Cl.
| | |
|---|---|
| *A01N 47/40* | (2006.01) |
| *A01N 25/30* | (2006.01) |
| *A01N 25/08* | (2006.01) |
| *A01N 25/04* | (2006.01) |
| *A01C 1/06* | (2006.01) |

(52) U.S. Cl.
CPC ............... *A01N 47/40* (2013.01); *A01C 1/06* (2013.01); *A01N 25/04* (2013.01); *A01N 25/08* (2013.01); *A01N 25/30* (2013.01)

(58) Field of Classification Search
CPC ......... A01N 47/40; A01N 25/04; A01N 25/30
See application file for complete search history.

(56) References Cited

U.S. PATENT DOCUMENTS

| | | |
|---|---|---|
| 5,238,904 A | 8/1993 | Frisch et al. |
| 2001/0008873 A1 | 7/2001 | Shafer et al. |
| 2006/0270559 A1 | 11/2006 | Maekawa et al. |
| 2012/0128750 A1 | 5/2012 | Finch |

FOREIGN PATENT DOCUMENTS

| | | |
|---|---|---|
| CN | 1993044 A | 7/2007 |
| EP | 2708122 A1 | 3/2014 |
| GB | 2149665 A | 6/1985 |
| JP | 60-104002 A | 6/1985 |
| JP | 04-312506 A | 11/1992 |
| JP | 2008-543891 A | 12/2008 |
| JP | 2012-051871 A | 3/2012 |
| WO | WO 2006/013972 A1 | 2/2006 |
| WO | WO 2006/024333 A2 | 3/2006 |
| WO | WO 2012/005371 A1 | 1/2012 |
| WO | WO 2015/029908 A1 | 3/2015 |

OTHER PUBLICATIONS

International Search Report dated Dec. 6, 2016, in PCT/JP2016/078594.
Office Action dated Jul. 31, 2017, in Taiwan Application No. 105131173, with English translation.
European Search Report for Appl. Ser. No. 16851616.9, dated Feb. 26, 2019, 10 pages.

*Primary Examiner* — Barbara P Badio
(74) *Attorney, Agent, or Firm* — Foley & Lardner LLP

(57) ABSTRACT

A composition including: (A) an aqueous agrochemically active compound such as acetamiprid; (B) a polyhydric alcohol; (C) a formalin condensate of sodium alkylnaphthalenesulfonate, or a modified styrene-maleic anhydride copolymer; (D) a thickener such as xanthan gum; (E) at least one inorganic particle selected from the group consisting of silica, montmorillonite and attapulgite; and (F) water.

6 Claims, No Drawings

AGROCHEMICAL COMPOSITION

CROSS-REFERENCE TO RELATED APPLICATIONS

This application is a National Stage application of PCT/JP2016/078594, filed Sep. 28, 2016, which claims priority from Japanese application JP 2015-192835, filed Sep. 30, 2015.

TECHNICAL FIELD

The present invention relates to an agrochemical composition. More specifically, the present invention relates to a composition that maintains favorable fluidity and hardly undergoes phase separation even during high temperature storage, even when it contains a water-soluble agrochemically active compound at a high concentration.

Priority is claimed on Japanese Patent Application No. 2015-192835, filed Sep. 30, 2015, the content of which is incorporated herein by reference.

BACKGROUND ART

An agrochemically active compound in a solid form at normal temperature is sometimes provided to farmers and the like as a preparation (flowable formulation such as an SC formulation) or the like which is finely pulverized and uniformly dispersed in water using a surfactant or the like. When an agrochemically active compound having a solubility in water of 100 mg/l or more which is in a form of solid at normal temperature (hereinafter referred to as a water-soluble agrochemically active compound) is used in a flowable formulation or the like, due to repetition of dissolution in water and precipitation from water of the water-soluble agrochemically active compound, the size of the dispersed particles of the water-soluble agrochemically active compound gradually increases, resulting in lowering of fluidity, phase separation, precipitation or the like in some cases.

In order to solve the growth phenomenon of the dispersed particles of the water-soluble agrochemically active compound as described above, for example, Patent Document 1 proposes an aqueous pest control suspension containing an agrochemical component having a solubility of 500 to 6,000 mg/l in water at 20° C., a polycarboxylate type surfactant, a sulfonate type surfactant and water.

Patent Document 2 proposes a composition containing an agrochemically active compound such as acetamiprid, an anionic surfactant such as alkylnaphthalenesulfonate and a naphthalene formaldehyde condensate, an inorganic solid carrier such as silica, attapulgite clay and bentonite clay, an antifreeze such as glycerol, a thickener such as xanthan gum, and water.

Patent Document 3 proposes a composition containing an agricultural chemical active ingredient such as acetamiprid, a styrene maleic anhydride copolymer, a polymer having a repeating unit derived from rosin, salicylic acid or a derivative thereof, and an elution controlling agent such as amorphous silicon dioxide (hydrophobic white carbon or the like), a water-soluble polymer and a surfactant (alkyl sulfonate formalin condensate or the like).

Patent Document 4 proposes a pest control composition in the form of an aqueous suspension containing flonicamid having a solubility in water at 20° C. of 5,200 mg/l, a polycarboxylic acid salt, a formalin condensate of sodium alkylnaphthalenesulfonate, a sulfonic acid type surfactant and water.

CITATION LIST

Patent Documents

[Patent Document 1] International Patent Publication No. 2012/005371
[Patent Document 2] Published Japanese Translation No. 2008-543891 of the PCT International Publication
[Patent Document 3] International Patent Publication No. 2006/013972
[Patent Document 4] International Patent Publication No. 2015/029908

SUMMARY OF INVENTION

Technical Problem

An object of the present invention is to provide a composition that maintains favorable fluidity and hardly undergoes phase separation even during high temperature storage, even when it contains a water-soluble agrochemically active compound at a high concentration.

Solution to Problem

As a result of intensive studies in order to solve the above problems, the inventors of the present invention have completed the present invention including the following embodiments.

[1] A composition including:
a water-soluble agrochemically active compound (component (A));
a polyhydric alcohol (component (B));
a formalin condensate of sodium alkylnaphthalenesulfonate, or a modified styrene-maleic anhydride copolymer (component (C));
a thickener (component (D));
at least one inorganic particle selected from the group consisting of silica, montmorillonite and attapulgite (component (E)); and
water (component (F)).

[2] The composition according to the above [1], wherein the component (A) has a solubility in water at 20° C. of 100 to 100,000 mg/l.

[3] The composition according to the above [1] or [2], wherein a content of the component (A) is from 1 to 50% by mass with respect to the mass of the composition.

[4] The composition according to the above [3],
wherein a content of the component (B) is from 6 to 40% by mass with respect to the mass of the composition,
a content of the component (C) is from 0.1 to 20% by mass with respect to the mass of the composition,
a content of the component (D) is from 0.01 to 2% by mass with respect to the mass of the composition,
a content of the component (E) is from 0.1 to 20% by mass with respect to the mass of the composition, and
a content of the component (F) is from 20 to 80% by mass with respect to the mass of the composition.

[5] The composition according to any one of the above [1] to [4], wherein the component (A) is acetamiprid.

[6] A method of treating a seed, including bringing the composition according to any one of the above [1] to [5] into contact with a seed.

[7] A method of allowing an agrochemically active compound to act on a plant, the method including spraying the composition according to any one of the above [1] to [5].

Advantageous Effects of Invention

The composition of the present invention maintains favorable fluidity and hardly undergoes phase separation even during high temperature storage, even when it contains a water-soluble agrochemically active compound at a high concentration.

DESCRIPTION OF EMBODIMENTS

A composition of the present invention includes: a water-soluble agrochemically active compound (component (A)); a polyhydric alcohol (component (B)); a formalin condensate of sodium alkylnaphthalenesulfonate, or a modified styrene-maleic anhydride copolymer (component (C)); a thickener (component (D)); at least one inorganic particle selected from the group consisting of silica, montmorillonite and attapulgite (component (E)); and water (component (F)).
(Component (A): Water-Soluble Agrochemically Active Compound)

The water-soluble agrochemically active compound is an agrochemically active compound which is solid at normal temperature and is slightly soluble in water. The water-soluble agrochemically active compound preferably has a solubility in water at 20° C. of 100 to 100,000 mg/l, and more preferably 1,000 to 10,000 mg/l. When the concentration of the agrochemically active compound to be contained in an agrochemical formulation is set to a value equal to or higher than the above solubility, dispersed particles of the water-soluble agrochemically active compound tend to gradually grow and increase in size due to repetition of dissolution in water and precipitation from water of the water-soluble agrochemically active compound. The problem to be solved by the present invention is to suppress such growth of particles. An agrochemically active compound is a compound approved as an agricultural chemical or a compound which may be approved.

The water-soluble agrochemically active compound is not particularly limited by its activity or action. For example, insecticidal activity, acaricidal activity, nematicidal activity, bactericidal activity, herbicidal activity, plant growth regulating activity and the like can be mentioned.

Specific examples of the water-soluble agrochemically active compound include compounds having an insecticidal activity, acaricidal activity or nematicidal activity such as (E)-N1-[(6-chloro-3-pyridyl)methyl]-N2-cyano-N1-methyl-acetamidine [common name: acetamiprid, solubility in water: 4,200 mg/l (25° C.)], 2,2-dimethyl-1,3-benzodioxol-4-yl-methylcarbamate hydrochloride [common name: bendiocarb, solubility in water: 28,000 mg/l (20° C., pH 7)], 2,2-dichlorovinyl dimethyl phosphate [common name: dichlorvos, solubility in water: 18,000 mg/l (25° C.)], 2-ethylthiomethylphenyl methyl carbamate [common name: ethiofencarb, solubility in water: 1,800 mg/l (20° C.)], 1-(6-chloro-3-pyridylmethyl)-N-nitroimidazolidin-2-ylideneamine [common name: imidacloprid, solubility in water: 480 mg/l (20° C.)], S-methyl-N-(methylcarbamoyloxy) thioacetimidate [common name: methomyl, solubility in water: 46,000 mg/l (20° C., pH 7)], and 1,3-dichloropropene [common name: D-D, solubility in water: 2,520 mg/l (E form, 20° C.), 2,450 mg/l (Z form, 20° C.)];

compounds having a bactericidal activity such as 1-(4-amino-1,2-dihydro-2-oxopyrimidin-1-yl)-4-[(S)-3-amino-5-(1-methyl-guanidino)valeramido]-1,2,3,4,-tetradioxy-β-D-erythrohexy-2-enopyranuronic acid [common name: blasticidin S, solubility in water: 30,000 mg/l (20° C.)], 1-(2-cyano-2-methoxyiminoacetyl)-3-ethylurea [common name: cymoxanil, solubility in water: 782 mg/l (20° C.)], 2-(4-chlorophenyl)-3-cyclopropyl-1-(1H-1,2,4-triazol-1-yl) butan-2-ol [common name: cyproconazole, solubility in water: 100 mg/l (20° C., pH 6.9)], 3,5-dimethyl-tetrahydro-2H-1,3,5-thiadiazine-2-thione [common name: dazomet, solubility in water: 3,500 mg/l (20° C.)], 5-butyl-2-dimethylamino-6-methylpyridin-4-ol [common name: dimethirimol, solubility in water: 1,200 mg/l (25° C.)], (Z)-2'-methylacetophenone-4,6-dimethylpyrimidin-2-yl hydrazone [common name: ferimzone, solubility in water: 208 mg/l (20° C.)], 5-methyl-1,2,4-triazolo [3,4-b] benzothiazole [common name: tricyclazole, solubility in water: 596 mg/l (20° C.)], and 1,2,5,6-tetrahydro [3,2,1-ij] quinolin-4-one [common name: pyroquilon, solubility in water: 4,600 mg/l (25° C.)];

compounds having a herbicidal activity such as 3-isopropyl-1H-2,1,3-benzothiadiazin-4(3H)-one-2,2-dioxide [common name: bentazon, solubility in water: 570 mg/l (20° C.)], 2-(1-cyano-1-methylamino)-4-ethylamino-6-chloro-1,3, 5-triazine [common name: cyanazine, solubility in water: 163 mg/l (20° C.)], 2-chloro-N-(2,4-dimethyl-3-thienyl)-N-(2-methoxy-1-methylethyl) acetamide [common name: dimethenamid, solubility in water: 1,610 mg/l (20° C.)], N-(phosphonomethyl) glycine isopropylamine salt [common name: glyphosate isopropylamine salt, solubility in water: 10,000 mg/l (20° C.)], and 3-(4,6-dimethoxy-1,3,5-triazin-2-yl)-1-[2-(2-methoxy-ethoxy)phenylsulfonyl] urea [common name: cinosulfuron, solubility in water: 4,000 mg/l (25° C., pH 6.7)]; and compounds having a plant growth regulating activity such as N-dimethyl succinic amino acid [common name: daminozide, solubility in water: 100,000 mg/l (25° C.)], and (RS)-2-(2,4-dichlorophenoxy) propionic acid triethanolamine salt [common name: dichlorprop, solubility in water: 590 mg/l (20° C.)].

One type of these water-soluble agrochemically active compounds can be used alone or two or more types can be used in combination.

The amount of the water-soluble agrochemically active compound that can be contained in the composition of the present invention is preferably from 1 to 50% by mass, more preferably from 5 to 40% by mass, and still more preferably from 10 to 40% by mass, with respect to the mass of the composition.
(Component (B): Polyhydric Alcohol)

The polyhydric alcohol is a compound having two or more hydroxyl groups, and is a compound having 2 to 30 carbon atoms (which can be described as a C2-C30 polyhydric alcohol). Examples thereof include compounds having two hydroxyl groups known as dihydric alcohols (which can be described as C2-C30 dihydric alcohols), compounds having three hydroxyl groups known as trihydric alcohols (which can be described as C2-C30 trihydric alcohols), and compounds having four hydroxyl groups known as tetrahydric alcohols (which can be described as C2-C30 tetrahydric alcohols).

Although it is not particularly limited as long as it is a polyhydric alcohol, examples of the dihydric alcohol include ethylene glycol, propylene glycol, diethylene glycol, triethylene glycol and hexylene glycol, examples of the trihydric alcohol include glycerol (aka: 1,2,3-propanetriol), 1,2,4-butanetriol and 1,2,5-pentanetriol, and examples of the tetrahydric alcohol include pentaerythritol and the like. Examples of alcohols having 5 or more valencies include polyglycerin and the like. It is preferably a trihydric alcohol, and more preferably glycerol.

Glycerol is a substance that may be contained as an antifreeze or the like in a conventionally known agrochemical formulation.

The amount of the polyhydric alcohol that can be contained in the composition of the present invention is preferably from 6 to 40% by mass, more preferably from 7 to 30% by mass, and still more preferably from 10 to 20% by mass, with respect to the mass of the composition.

(Component (C): Formalin Condensate of Sodium Alkylnaphthalenesulfonate or Modified Styrene-Maleic Anhydride Copolymer)

The formalin condensate of sodium alkylnaphthalenesulfonate is a compound known as one type of anionic surfactant. The formalin condensate of sodium alkylnaphthalenesulfonate is formed by methylene condensation with formalin based on the structure of alkylnaphthalenesulfonate. Examples of the commercially available formalin condensate of sodium alkylnaphthalenesulfonate include Morwet D 425 (manufactured by Akzo Nobel N.V.), TERSPERSE 2020 (manufactured by Huntsman International LLC) and Agrosurf WG-2300 (manufactured by Takemoto Oil & Fat Co., Ltd.).

The modified styrene-maleic anhydride copolymer is a copolymer of modified styrene and maleic anhydride, and TERSPERSE 2612 (manufactured by Huntsman International LLC) or the like can be exemplified.

The amount of the formalin condensate of sodium alkylnaphthalenesulfonate or the modified styrene-maleic anhydride copolymer which can be contained in the composition of the present invention is preferably from 0.1 to 20% by mass, more preferably from 1 to 10% by mass, and still more preferably from 1 to 5% by mass, with respect to the mass of the composition.

(Component (D): Thickener)

A thickener is a polymer compound that can increase the viscosity of an aqueous solution or suspension. Examples of the thickener include starch, dextrin, cellulose, methyl cellulose, ethyl cellulose, carboxymethyl cellulose, hydroxyethyl cellulose, hydroxypropyl cellulose, carboxymethyl starch, pullulan, sodium alginate, ammonium alginate, propylene glycol alginate ester, guar gum, locust bean gum, gum arabic, xanthan gum, gelatin, casein, polyvinyl alcohol, polyethylene oxide, polyethylene glycol, ethylene/propylene block polymers, sodium polyacrylate, polyvinyl pyrrolidone and carrageenan.

One type of these thickeners can be used alone or two or more types can be used in combination.

The amount of the thickener which can be contained in the composition of the present invention is preferably from 0.01 to 2% by mass, more preferably from 0.05 to 1% by mass, and still more preferably from 0.05 to 0.5% by mass, with respect to the mass of the composition.

(Component (E): Inorganic Particle)

The component (E) (inorganic particle) used in the present invention is at least one selected from the group consisting of silica, montmorillonite and attapulgite.

Examples of the silica include fumed silica and precipitated silica.

Fumed silica is amorphous silica synthesized by a combustion method. As a combustion method, for example, a combustion hydrolysis method of silicon tetrachloride can be mentioned. The fumed silica used in the present invention preferably has a volume average particle diameter or an average primary particle diameter of 100 nm or less. The fumed silica used in the present invention may be hydrophilic silica or hydrophobic silica.

Examples of commercially available hydrophilic fumed silica include WACKER HDK H15 (manufactured by Wacker Asahikasei Silicone Co., Ltd.), AEROSIL 200 (manufactured by Nippon Aerosil Co., Ltd.), AEROSIL 50 (manufactured by Nippon Aerosil Co., Ltd.), and REOLOSIL QS-10 (manufactured by Tokuyama Corporation).

Examples of commercially available hydrophobic fumed silica include WACKER HDK V15 (manufactured by Wacker Asahikasei Silicone Co., Ltd.), AEROSIL R 972 (manufactured by Nippon Aerosil Co., Ltd.), AEROSIL R 104 (manufactured by Nippon Aerosil Co., Ltd.), AEROSIL RX 200 (manufactured by Nippon Aerosil Co., Ltd.) and REOLOSIL MT-10 (manufactured by Tokuyama Corporation). The hydrophobic fumed silica is preferably hydrophobized, for example, with a silicone-based compound (see Japanese Unexamined Patent Application, First Publication No. Sho 61-23666 or the like).

Precipitated silica is silica synthesized in water or in an organic solvent such as an alcohol.

Examples of commercially available precipitated silica include DUROSIL (manufactured by DSL. Japan Co., Ltd.), EXTRUSIL (manufactured by DSL. Japan Co., Ltd.), CARPLEX #100 (manufactured by DSL. Japan Co., Ltd.), CARPLEX #1120 (manufactured by DSL. Japan Co., Ltd.), CARPLEX #80 (manufactured by DSL. Japan Co., Ltd.), CARPLEX CS-8 (manufactured by DSL. Japan Co., Ltd.), CARPLEX FPS-3 (manufactured by DSL. Japan Co., Ltd.), CARPLEX XR (manufactured by DSL. Japan Co., Ltd.), TOKUSIL AL-1 (manufactured by Tokuyama Corporation), TOKUSIL NSK (manufactured by Tokuyama Corporation), TOKUSIL P (manufactured by Tokuyama Corporation), NIPSIL G 300 (manufactured by Nippon Silica Industries Co., Ltd.), NIPSIL NA (manufactured by Nippon Silica Industries Co., Ltd.), NIPSIL NS-K (manufactured by Nippon Silica Industries Co., Ltd.) and NIPSIL NS-KR (manufactured by Nippon Silica Industries Co., Ltd.).

Montmorillonite is a layered silicate mineral belonging to the smectite group. The montmorillonite used in the present invention preferably has a volume average particle diameter of 10 nm to 10 μm. As commercially available montmorillonite, KUNIPIA F (manufactured by Kunimine Industries Co., Ltd.) and the like can be mentioned.

Attapulgite is a magnesium/aluminum-based silicate mineral. The attapulgite used in the present invention preferably has a volume average particle diameter of 10 nm to 10 μm. As commercially available attapulgite, Attagel 50 (manufactured by Hayashi Kasei Co., Ltd.) and the like can be mentioned.

Any one of these silica, montmorillonite or attapulgite may be used alone or two or more types thereof may be used in combination.

The amount of at least one inorganic particle selected from the group consisting of silica, montmorillonite and attapulgite which can be contained in the composition of the present invention is preferably from 0.1 to 20% by mass, more preferably from 0.1 to 10% by mass, and still more preferably from 0.2 to 5% by mass, with respect to the mass of the composition.

(Component (F): Water)

The water used in the present invention is not limited by hardness, and it may be soft water or hard water. Examples of water used in the present invention include agricultural water, industrial water, tap water and distilled water.

The amount of water that can be contained in the composition of the present invention is preferably from 20 to 80% by mass, more preferably from 30 to 75% by mass, and still more preferably from 40 to 70% by mass, with respect to the mass of the composition.

(Preferred Range)

In the present invention, the components (A) to (F) can be limited to any mass range, unless the total of the composition exceeds 100% by mass. The limitation by the mass of the composition of the present invention can be carried out by arbitrarily combining preferred masses described for each component. In a particularly preferred limitation by the mass of the composition, the content of the component (A) is from 1 to 50% by mass with respect to the mass of the composition, and moreover, the content of the component (B) is from 6 to 40% by mass with respect to the mass of the composition, the content of the component (C) is from 0.1 to 20% by mass with respect to the mass of the composition, the content of the component (D) is from 0.01 to 2% by mass with respect to the mass of the composition, the content of the component (E) is from 0.1 to 20% by mass with respect to the mass of the composition, and the content of the component (F) is from 20 to 80% by mass with respect to the mass of the composition.

In a still more preferred limitation by the mass of the composition, the content of the component (A) is from 5 to 40% by mass with respect to the mass of the composition, the content of the component (B) is from 7 to 30% by mass with respect to the mass of the composition, the content of the component (C) is from 1 to 10% by mass with respect to the mass of the composition, the content of the component (D) is from 0.05 to 1% by mass with respect to the mass of the composition, the content of the component (E) is from 0.1 to 10% by mass with respect to the mass of the composition, and the content of the component (F) is from 30 to 75% by mass with respect to the mass of the composition.

In a still more preferred limitation by the mass of the composition, the content of the component (A) is from 10 to 40% by mass with respect to the mass of the composition, the content of the component (B) is from 10 to 20% by mass with respect to the mass of the composition, the content of the component (C) is from 1 to 5% by mass with respect to the mass of the composition, the content of the component (D) is from 0.05 to 0.5% by mass with respect to the mass of the composition, the content of the component (E) is from 0.2 to 5% by mass with respect to the mass of the composition, and the content of the component (F) is from 40 to 70% by mass with respect to the mass of the composition.

The composition of the present invention may further contain other components. As other components, surfactants other than the component (C), pigments, dyes, antifoaming agents, antiseptics and the like can be mentioned.

The content of other components is preferably from 0 to 10% by mass, more preferably from 0 to 5% by mass, and still more preferably from 0.1 to 4% by mass, with respect to the mass of the composition.

Examples of surfactants other than the component (C) include sugar ester-type surfactants such as sorbitan fatty acid esters (C12 to C18), POE sorbitan fatty acid esters (C12 to C18) and sucrose fatty acid esters; fatty acid ester-type surfactants such as POE fatty acid esters (C12 to C18), POE resin acid esters and POE fatty acid diesters (C12 to C18); alcohol-type surfactants such as POE alkyl ethers (C12 to C18); alkylphenol-type surfactants such as POE alkyl (C8 to C12) phenyl ethers, POE dialkyl (C8 to C12) phenyl ethers and POE alkyl (C8 to C12) phenyl ether formalin condensates; polyoxyethylene/polyoxypropylene block polymer-type surfactants such as polyoxyethylene/polyoxypropylene block polymers and alkyl (C12 to C18) polyoxyethylene/polyoxypropylene block polymer ethers; alkylamine-type surfactants such as POE alkylamines (C12 to C18) and POE fatty acid amides (C12 to C18); bisphenol-type surfactants such as POE fatty acid bisphenyl ethers; polyaromatic ring-type surfactants such as POA benzyl phenyl (or phenyl phenyl) ethers and POA styryl phenyl (or phenyl phenyl) ethers; nonionic surfactants including silicone-based and fluorine-based surfactants such as POE ethers and ester-type silicon and fluorine-based surfactants, and vegetable oil-type surfactants such as POE castor oil and POE hydrogenated castor oil; sulfate-type surfactants such as alkyl sulfates (C12 to C18, Na, $NH_4$, alkanolamine), POE alkyl ether sulfates (C12 to C18, Na, $NH_4$, alkanolamine), POE alkylphenyl ether sulfates (C12 to C18, $NH_4$, alkanolamine, Ca), POE benzyl (or styryl) phenyl (or phenyl phenyl) ether sulfates (Na, $NH_4$, alkanolamine) and polyoxyethylene/polyoxypropylene block polymer sulfates (Na, $NH_4$, alkanolamine); sulfonate-type surfactants such as paraffin (alkane) sulfonates (C12 to C22, Na, Ca, alkanolamine), AOS (C14 to C16, Na, alkanolamine), dialkylsulfosuccinate (C8 to C12, Na, Ca, Mg), alkylbenzene sulfonates (C12, Na, Ca, Mg, $NH_4$, alkylamine, alkanol, amine, cyclohexylamine), mono- or dialkyl (C3 to C6) naphthalene sulfonates (Na, $NH_4$, alkanolamine, Ca, Mg), alkyl (C8 to C12) diphenylether disulfonate (Na, $NH_4$), lignin sulfonate (Na, Ca), POE alkyl (C8 to C12) phenyl ether sulfonates (Na) and POE alkyl (C12 to C18) ether sulfosuccinic acid half esters (Na); POE alkyl (C12 to C18) ether phosphates (Na, alkanolamine) such as carboxylic acid-type fatty acid salts (C12 to C18, Na, K, $NH_4$, alkanolamine), N-methyl fatty acid sarcosinates (C12 to C18, Na) and resin acid salts (Na, K); and anionic surfactants including phosphate-type surfactants such as POE mono- or dialkyl (C8 to C12) phenyl ether phosphates (Na, alkanolamine), POE benzyl (or styryl) phenyl (or phenylphenyl) ether phosphates (Na, alkanolamine), phosphatidylcholine/phosphatidylethanolimine (lecithin) and alkyl (C8 to C12) phosphates.

The content of the surfactant other than the component (C) is preferably from 0 to 10% by mass, more preferably from 0 to 5% by mass, and still more preferably from 1 to 3% by mass, with respect to the mass of the composition.

Examples of pigments or dyes include inorganic pigments such as ochre, zinc chromate, lead chromate, ultramarine blue, iron blue, red iron oxide, aluminum hydroxide, carbon black and graphite; and organic dyes and pigments such as azo pigments, azo disperse dyes, phthalocyanine pigments and anthraquinone disperse dyes.

The content of the pigment or dye is preferably from 0 to 1% by mass, more preferably from 0 to 0.5% by mass, and still more preferably from 0.01 to 0.1% by mass, with respect to the mass of the composition.

Examples of the antifoaming agent include Silicone SM 5512 (manufactured by Dow Corning Toray Silicone Co., Ltd.), Antifoam E-20 (manufactured by Kao Corporation) and SILFOAM SE 39 (manufactured by Wacker Asahikasei Silicone Co., Ltd.).

The content of the antifoaming agent is preferably from 0 to 5% by mass, more preferably from 0 to 1% by mass, and still more preferably from 0.1 to 0.5% by mass, with respect to the mass of the composition.

Examples of the antiseptic include isothiazoline-based antiseptics such as methylisothiazolinone (MIT, MI), chloromethylisothiazolinone (CMIT, CMI), octylisothiazolinone (OIT, OI), dichlorooctylisothiazolinone (DCOIT, DCOI) and benzisothiazolinone (BIT), hexamethylenetetramine, sodium propionate, sorbic acid, aqueous sulfurous acid, paraformaldehyde, benzoic acid, propyl p-hydroxybenzoate, methyl p-hydroxybenzoate, sodium benzoate, ascorbic acid, ascorbyl palmitate, sodium=1,1'-biphenyl-2-olate, and the like. Further, examples of commercially available antiseptics include Legend MK (manufactured by Rohm and Haas Company), Denicide BIT-20N (manufactured by Nagase ChemteX Corporation), Proxel GXL (manufactured by Avecia Inc.) and KATHON CG (manufactured by The Dow Chemical Company).

The content of the antiseptic is preferably from 0 to 5% by mass, more preferably from 0.01 to 1% by mass, and still more preferably from 0.05 to 0.5% by mass, with respect to the mass of the composition.

The composition of the present invention can be obtained in the same manner as the conventional method for producing a preparation such as an SC formulation. The composition of the present invention can be obtained, for example, by mixing predetermined amounts of the components (A) to (F), followed by wet grinding to pulverize the particles of the component (A), or by mixing predetermined amounts of the components (A) to (C) and (E) to (F), followed by wet grinding to pulverize the particles of the component (A), and then adding and mixing the component (D). The volume average particle size of the pulverized component (A) contained in the composition of the present invention is preferably from 0.1 to 20 µm, more preferably from 0.5 to 20 µm, and still more preferably from 0.5 to 15 µm.

The volume average particle diameter is a value obtained by the measurement without distinguishing primary particles, primary aggregates (aggregates), and secondary aggregates (agglomerates). For the measurement of the volume average particle diameter, a laser diffraction-type particle size distribution measuring apparatus SALD-2200 manufactured by Shimadzu Corporation can be used.

Wet grinding can be carried out using, for example, a bead mill, a sand mill or the like. Since the molecular structure of the component (D) may break in some cases by wet grinding, it is preferable to wet-grind constituents other than the component (D), and then add and mix the component (D).

The application method of the composition of the present invention is not particularly limited. For example, the composition of the present invention can be sprayed on the ground or sprayed in the air as it is or by diluting it with water to a predetermined concentration so as to bring the component (A) into contact with soil, plants and the like. The ground application may be carried out by a hand sprayer, a power sprayer, a boom sprayer, a sprinkler, a mist sprayer, a speed sprayer or the like. The aerial application may be carried out by a radio controlled helicopter, a helicopter, an airplane, or the like. Further, seeds can be impregnated or coated with the component (A) by using the composition of the present invention as it is or by diluting it with water to a predetermined concentration and immersing the seeds therein. Furthermore, it can also be used for the irrigation to a nursery box, the culture solution for hydroponic cultivation, the injection into stems, and the like. In the above application method, the composition of the present invention may be used alone or by mixing with another agrochemical composition.

EXAMPLES

Hereinafter, the present invention will be described in more detail by showing Examples. However, the present invention is in no way limited by the following examples. Additions, omissions, substitutions, and other modifications in the constitution can be made without departing from the spirit or scope of the present invention.

Among the materials used in the present example, those requiring particular explanations are shown below.

Water-soluble agrochemically active compound I: Acetamiprid

Surfactant I: Morwet D 425 (formalin condensate of sodium alkylnaphthalenesulfonate, manufactured by Akzo Nobel Co., Ltd.)

Surfactant II: Newkalgen C-314 (POE tristyrylphenyl ether, manufactured by Takemoto Oil & Fat Co., Ltd.)

Surfactant III: Newkalgen BX-C (sodium salt of alkylnaphthalene sulfonic acid, manufactured by Takemoto Oil & Fat Co., Ltd.)

Surfactant IV: Newkalgen EX-70 (sodium salt of dialkylsulfosuccinic acid, manufactured by Takemoto Oil & Fat Co., Ltd.)

Surfactant V: Newkalgen SX-C (sodium salt of alkylbenzene sulfonic acid, manufactured by Takemoto Oil & Fat Co., Ltd.)

Surfactant VI: Newkalgen LX-C (sodium salt of alkyl sulfuric acid, manufactured by Takemoto Oil & Fat Co., Ltd.)

Surfactant VII: Newkalgen PS-P (formalin condensate of sodium naphthalene sulfonate, manufactured by Takemoto Oil & Fat Co., Ltd.)

Surfactant VIII: TERSPERSE 2612 (40-50% modified styrene/maleic anhydride copolymer and 50-60% dipropylene glycol monoethyl ether (Huntsman Japan KK))

Fumed silica I: Aerosil R 972; (hydrophobic, average diameter of primary particles: about 16 nm, manufactured by Nippon Aerosil Co., Ltd.)

Fumed silica II: Aerosil 200 (hydrophilic, average diameter of primary particles: about 12 nm, manufactured by Nippon Aerosil Co., Ltd.)

Clay mineral I: Kunipia F (montmorillonite, volume average particle diameter: about 2,000 nm, manufactured by Kunimine Industries Co., Ltd.)

Clay mineral II: Attagel 50 (attapulgite, volume average particle size: about 100 nm, manufactured by Hayashi Kasei Co., Ltd.)

Precipitated silica I: SIPERNAT D 13 (hydrophobic, volume average particle diameter: about 9,500 nm, manufactured by Degussa AG)

Precipitated silica II: Carplex #101 (hydrophilic, volume average particle diameter: about 10,500 nm, manufactured by DSL. Japan Co., Ltd.)

Alumina: AEROXIDE Alu C (average diameter of primary particles: about 13 nm, manufactured by Nippon Aerosil Co., Ltd.)

Example 1

30 parts by mass of the water-soluble agrochemically active compound I, 15 parts by mass of glycerol, 2 parts by mass of the surfactant I, 2 parts by mass of the surfactant II, 2 parts by mass of the fumed silica I, 0.2 parts by mass of an antifoaming agent, and 33.8 parts by mass of water were mixed to obtain a mixture solution.

30 g of the above mixture solution and 30 g of glass beads (φ: 1.0 to 1.4 mm) were placed in a 45 cc container made of agate of a planetary ball mill (Pulverisette 7, manufactured by Fritsch GmbH) and pulverized at 800 rpm for 5 minutes to obtain a pulverized liquid. In order to remove the glass beads from the above pulverized liquid, the slurry was sucked up with a Pasteur pipette (tip inner diameter: about 0.5 mm) and transferred to a separate container. The slurry had the same level of viscosity as that of the mixture solution.

A solution formed by mixing 0.2 part by mass of a thickener (xanthan gum), 0.1 parts by mass of an antiseptic and 14.7 parts by mass of water was added to 85 parts by mass of the slurry and mixed to obtain a composition 1. The volume average particle diameter of the water-soluble agrochemically active compound I in the composition 1 was 3.5 μm.

(Degree of Phase Separation, Phase Separation)

The composition was placed in a 20 ml transparent vial bottle, and the bottle was capped and left to stand at 54° C. for 7 days. Thereafter, the composition in the vial bottle was observed. A distance L1 from the liquid surface to the boundary (interface) between the two phases that had undergone phase separation and a distance L0 from the liquid surface to the bottom of the bottle were measured, and the degree of phase separation (%) was calculated by the following formula to evaluate the degree of phase separation by the following index (hereinafter, this index is sometimes referred to as phase separation).

$$\text{Degree of phase separation (\%)} = L1 \text{ (mm)}/L0 \text{ (mm)} \times 100$$

A: Degree of phase separation of 0% or more and less than 5%

B: Degree of phase separation of 5% or more and less than 30%

D: Degree of phase separation of 30% or more (Fluidity)

The composition was placed in a 20 ml transparent vial bottle, and the bottle was capped and left to stand at 54° C. for 7 days. Thereafter, the composition in the vial bottle was observed with the naked eye when the vial bottle was tilted, and the fluidity was evaluated according to the following criteria.

A: When tilted, the composition in the bottle quickly flowed.

B: When tilted, the composition in the bottle slowly flowed.

C: When tilted, the composition in the bottle flowed slightly.

D: When tilted, the composition in the bottle did not flow.

The evaluation results of the phase separation and fluidity for the composition 1 are shown in Table 1.

Example 2

A composition 2 was obtained in the same manner as in Example 1 except that 30 parts by mass of the water-soluble agrochemically active compound I was replaced by 10 parts by mass of the water-soluble agrochemically active compound I and 20 parts by mass of water. The slurry as an intermediate product had the same level of viscosity as that of the mixture solution. The phase separation and fluidity for the composition 2 were evaluated in the same manner as in Example 1. The results are shown in Table 1. The volume average particle diameter of the water-soluble agrochemically active compound I in the composition 2 was 5.2 μm.

Example 3

A composition 3 was obtained in the same manner as in Example 1 except that the fumed silica I was replaced by the fumed silica II. The slurry as an intermediate product had the same level of viscosity as that of the mixture solution. The phase separation and fluidity for the composition 3 were evaluated in the same manner as in Example 1. The results are shown in Table 1. The volume average particle diameter of the water-soluble agrochemically active compound I in the composition 3 was 9.5 μm.

Example 4

A composition 4 was obtained in the same manner as in Example 1 except that the fumed silica I was replaced by the clay mineral I. The slurry as an intermediate product had the same level of viscosity as that of the mixture solution. The phase separation and fluidity for the composition 4 were evaluated in the same manner as in Example 1. The results are shown in Table 1. The volume average particle diameter of the water-soluble agrochemically active compound I in the composition 4 was 7.7 μm.

Example 5

A composition 5 was obtained in the same manner as in Example 1 except that the fumed silica I was replaced by the clay mineral II. The slurry as an intermediate product had the same level of viscosity as that of the mixture solution. The phase separation and fluidity for the composition 5 were evaluated in the same manner as in Example 1. The results are shown in Table 1. The volume average particle diameter of the water-soluble agrochemically active compound I in the composition 5 was 11.4 μm.

Example 6

A composition 6 was obtained in the same manner as in Example 1 except that glycerol was replaced by propylene glycol. The slurry as an intermediate product had the same level of viscosity as that of the mixture solution. The phase separation and fluidity for the composition 6 were evaluated in the same manner as in Example 1. The results are shown in Table 1. The volume average particle diameter of the water-soluble agrochemically active compound I in the composition 6 was 4.0 μm.

Example 7

A composition 7 was obtained in the same manner as in Example 1 except that the fumed silica I was replaced by the precipitated silica I. The slurry as an intermediate product had the same level of viscosity as that of the mixture solution. The phase separation and fluidity for the composition 7 were evaluated in the same manner as in Example 1. The results are shown in Table 1. The volume average particle diameter of the water-soluble agrochemically active compound I in the composition 7 was 5.9 μm.

Example 8

A composition 8 was obtained in the same manner as in Example 1 except that the fumed silica I was replaced by the precipitated silica II. The slurry as an intermediate product had the same level of viscosity as that of the mixture solution. The phase separation and fluidity for the composition 8 were evaluated in the same manner as in Example 1. The results are shown in Table 1. The volume average particle diameter of the water-soluble agrochemically active compound I in the composition 8 was 4.3 μm.

Example 9

A composition 9 was obtained in the same manner as in Example 1 except that the surfactant I was replaced by the surfactant Viii. The slurry as an intermediate product had the same level of viscosity as that of the mixture solution. The phase separation and fluidity for the composition 9 were evaluated in the same manner as in Example 1. The results are shown in Table 1. The volume average particle diameter of the water-soluble agrochemically active compound I in the composition 9 was 3.0 μm.

Example 10

A composition 10 was obtained in the same manner as in Example 1 except that glycerol was replaced by ethylene glycol. The slurry as an intermediate product had the same level of viscosity as that of the mixture solution. The phase separation and fluidity for the composition 10 were evaluated in the same manner as in Example 1. The results are shown in Table 1. The volume average particle diameter of the water-soluble agrochemically active compound I in the composition 10 was 6.4 μm.

Example 11

A composition 11 was obtained in the same manner as in Example 1 except that glycerol was replaced by diethylene glycol. The slurry as an intermediate product had the same level of viscosity as that of the mixture solution. The phase separation and fluidity for the composition 11 were evaluated in the same manner as in Example 1. The results are shown in Table 1. The volume average particle diameter of the water-soluble agrochemically active compound I in the composition 11 was 8.7 μm.

Example 12

A composition 12 was obtained in the same manner as in Example 1 except that glycerol was replaced by triethylene glycol. The slurry as an intermediate product had the same level of viscosity as that of the mixture solution. The phase separation and fluidity for the composition 12 were evaluated in the same manner as in Example 1. The results are shown in Table 1. The volume average particle diameter of the water-soluble agrochemically active compound I in the composition 12 was 5.9 μm.

Example 13

A composition 13 was obtained in the same manner as in Example 1 except that glycerol was replaced with polyglycerol #310 (manufactured by Sakamoto Yakuhin Kogyo Co., Ltd.). The slurry as an intermediate product had the same level of viscosity as that of the mixture solution. The phase separation and fluidity for the composition 13 were evaluated in the same manner as in Example 1. The results are shown in Table 1. The volume average particle diameter of the water-soluble agrochemically active compound I in the composition 13 was 5.6 μm.

Comparative Example 1

A composition 14 was obtained in the same manner as in Example 1 except that the surfactant I was replaced by the surfactant III. The slurry as an intermediate product had a higher viscosity than that of the mixture solution. The phase separation and fluidity for the composition 14 were evaluated in the same manner as in Example 1. The results are shown in Table 1. The volume average particle diameter of the water-soluble agrochemically active compound I in the composition 14 was 10.6 μm.

Comparative Example 2

Although an attempt was made to obtain a composition 15 in the same manner as in Example 1 except that the surfactant I was replaced by the surfactant IV, the viscosity of the slurry as an intermediate product was too high, and it could not be transferred to a separate container with a Pasteur pipette (tip inner diameter: about 0.5 mm).

Comparative Example 3

Although an attempt was made to obtain a composition 16 in the same manner as in Example 1 except that the surfactant I was replaced by the surfactant V, the viscosity of the slurry as an intermediate product was too high, and it could not be transferred to a separate container with a Pasteur pipette (tip inner diameter: about 0.5 mm).

Comparative Example 4

Although an attempt was made to obtain a composition 17 in the same manner as in Example 1 except that the surfactant I was replaced by the surfactant VI, the viscosity of the slurry as an intermediate product was too high, and it could not be transferred to a separate container with a Pasteur pipette (tip inner diameter: about 0.5 mm).

Comparative Example 5

Although an attempt was made to obtain a composition 18 in the same manner as in Example 1 except that the surfactant I was replaced by the surfactant VII, the viscosity of the slurry as an intermediate product was too high, and it could not be transferred to a separate container with a Pasteur pipette (tip inner diameter: about 0.5 mm).

Comparative Example 6

A composition 19 was obtained in the same manner as in Example 1 except that the fumed silica I was replaced by alumina. The slurry as an intermediate product had the same level of viscosity as that of the mixture solution. The phase separation and fluidity for the composition 19 were evaluated in the same manner as in Example 1. The results are shown in Table 1. The volume average particle diameter of the water-soluble agrochemically active compound I in the composition 19 was 13.7 μm.

Comparative Example 7

A composition 20 was obtained in the same manner as in Example 1 except that the fumed silica I was replaced by titanium oxide. The slurry as an intermediate product had the same level of viscosity as that of the mixture solution. The phase separation and fluidity for the composition 20 were evaluated in the same manner as in Example 1. The results are shown in Table 1. The volume average particle diameter of the water-soluble agrochemically active compound I in the composition 20 was 4.2 μm.

Comparative Example 8

A composition 21 was obtained in the same manner as in Example 1 except that 2 parts by mass of the fumed silica I was replaced by 2 parts by mass of water. The slurry as an intermediate product had the same level of viscosity as that of the mixture solution. The phase separation and fluidity for the composition 21 were evaluated in the same manner as in Example 1. The results are shown in Table 1. The volume average particle diameter of the water-soluble agrochemically active compound I in the composition 21 was 3.6 μm.

Comparative Example 9

A composition 22 was obtained in the same manner as in Example 1 except that 0.2 parts by mass of xanthan gum was replaced by 0.2 parts by mass of water. The slurry as an intermediate product had the same level of viscosity as that of the mixture solution. The phase separation and fluidity for the composition 22 were evaluated in the same manner as in Example 1. The results are shown in Table 1. The volume average particle diameter of the water-soluble agrochemically active compound I in the composition 22 was 3.7 μm.

Comparative Example 10

A composition 23 was obtained in the same manner as in Example 1 except that 2 parts by mass of the surfactant I was replaced by 2 parts by mass of water and 0.2 parts by mass of xanthan gum was replaced by 0.2 parts by mass of water. The slurry as an intermediate product had a higher viscosity than that of the mixture solution. The phase separation and fluidity for the composition 23 were evaluated in the same manner as in Example 1. The results are shown in Table 1. The volume average particle diameter of the water-soluble agrochemically active compound I in the composition 23 was 12.8 μm.

Comparative Example 11

A composition 24 was obtained in the same manner as in Example 1 except that glycerol was replaced by ethanol. The slurry as an intermediate product had the same level of viscosity as that of the mixture solution. The phase separation and fluidity for the composition 24 were evaluated in the same manner as in Example 1. The results are shown in Table 1. The volume average particle diameter of the water-soluble agrochemically active compound I in the composition 24 was 6.1 μm.

Comparative Example 12

A composition 25 was obtained in the same manner as in Example 1 except that glycerol was replaced by 2-propanol. The slurry as an intermediate product had the same level of viscosity as that of the mixture solution. The phase separation and fluidity for the composition 25 were evaluated in the same manner as in Example 1. The results are shown in Table 1. The volume average particle diameter of the water-soluble agrochemically active compound I in the composition 25 was 6.0 μm.

Comparative Example 13

A composition 26 was obtained in the same manner as in Example 1 except that glycerol was replaced by N-methylpyrrolidone. The slurry as an intermediate product had the same level of viscosity as that of the mixture solution. The phase separation and fluidity for the composition 26 were evaluated in the same manner as in Example 1. The results are shown in Table 1. The volume average particle diameter of the water-soluble agrochemically active compound I in the composition 26 was 9.3 μm.

Comparative Example 14

A composition 27 was obtained in the same manner as in Example 1 except that glycerol was replaced by γ-butyrolactone. The slurry as an intermediate product had the same level of viscosity as that of the mixture solution. The phase separation and fluidity for the composition 27 were evaluated in the same manner as in Example 1. The results are shown in Table 1. The volume average particle diameter of the water-soluble agrochemically active compound 1 in the composition 27 was 14.3 μm.

TABLE 1

|  | Phase separation | Fluidity |
| --- | --- | --- |
| Example 1 | A | A |
| Example 2 | A | A |
| Example 3 | A | A |
| Example 4 | A | A |
| Example 5 | A | A |
| Example 6 | A | B |
| Example 7 | B | B |
| Example 8 | B | B |
| Example 9 | A | A |
| Example 10 | A | B |
| Example 11 | A | B |
| Example 12 | A | B |
| Example 13 | A | A |
| Comparative Example 1 | A | D |
| Comparative Example 6 | A | D |
| Comparative Example 7 | D | D |
| Comparative Example 8 | D | D |
| Comparative Example 9 | D | D |
| Comparative Example 10 | D | D |
| Comparative Example 11 | D | C |
| Comparative Example 12 | B | C |
| Comparative Example 13 | D | B |
| Comparative Example 14 | D | C |

As shown in Comparative Examples 1 to 5, when the surfactant I was replaced by the surfactants III to VII, the viscosity became high, and in Comparative Examples 2 to 5, the glass beads could not be removed. As shown in Comparative Examples 6 to 7, when the fumed silica was replaced by alumina or titanium oxide, the phase separation increased or the fluidity deteriorated. As shown in Comparative Examples 8 to 10, unless at least one of the component (C), the component (D) or the component (E) was contained, the degree of phase separation increased and the fluidity deteriorated. As shown in Comparative Examples 11 to 14, when a monohydric alcohol or a water-soluble solvent having no alcohol group was used without using a polyhydric alcohol, the degree of phase separation increased. On the other hand, as shown in Examples 1 to 13, the present invention has a low degree of phase separation and excellent fluidity even during high temperature storage.

INDUSTRIAL APPLICABILITY

It is possible to provide a composition that maintains favorable fluidity and hardly undergoes phase separation even during high temperature storage, even when it contains a water-soluble agrochemically active compound at a high concentration.

The invention claimed is:

1. A composition comprising:
a water-soluble agrochemically active compound having a solubility in water at 20° C. of 100 to 100,000 mg/l (component (A));
a polyhydric alcohol having 2 to 30 carbon atoms selected from glycerol, ethylene glycol, diethylene glycol, triethylene glycol, and polyglycerol (component (B));
a formalin condensate of sodium alkylnaphthalenesulfonate (component (C));
a thickener (component (D));
at least one inorganic particle selected from the group consisting of silica, montmorillonite and attapulgite (component (E)); and
water (component (F)).

2. The composition according to claim 1, wherein a content of the component (A) is from 1 to 50% by mass with respect to the mass of the composition.

3. The composition according to claim 2,
wherein a content of the component (B) is from 6 to 40% by mass with respect to the mass of the composition,
a content of the component (C) is from 0.1 to 20% by mass with respect to the mass of the composition,
a content of the component (D) is from 0.01 to 2% by mass with respect to the mass of the composition,
a content of the component (E) is from 0.1 to 20% by mass with respect to the mass of the composition, and
a content of the component (F) is from 20 to 80% by mass with respect to the mass of the composition.

4. The composition according to claim 1, wherein the component (A) is acetamiprid.

5. A method of treating a seed comprising bringing the composition according to claim 1 into contact with a seed.

6. A method of allowing an agrochemically active compound to act on a plant, the method comprising spraying the composition according to claim 1.

* * * * *